United States Patent [19]
Kidwell

[11] Patent Number: 5,466,578
[45] Date of Patent: Nov. 14, 1995

[54] SURFACTANT-ENHANCED LIGHT EMISSION- OR ABSORBANCE-BASED BINDING ASSAYS FOR POLYNUCLEIC ACIDS

[75] Inventor: David A. Kidwell, Alexandria, Va.

[73] Assignee: The United States of America as represented by the Secretary of the Navy, Washington, D.C.

[21] Appl. No.: 280,537

[22] Filed: Jul. 26, 1994

Related U.S. Application Data

[63] Continuation-in-part of Ser. No. 4,009, Jan. 15, 1993, Pat. No. 5,332,659, which is a continuation-in-part of Ser. No. 865,526, Apr. 9, 1992, Pat. No. 5,314,802.

[51] Int. Cl.⁶ ............................. C12Q 1/68; G01N 21/64
[52] U.S. Cl. ............................ 435/6; 436/164; 436/172; 935/77; 935/78
[58] Field of Search ................................... 435/6; 935/77, 935/78; 436/164, 172

[56] References Cited

U.S. PATENT DOCUMENTS

| | | | |
|---|---|---|---|
| 5,279,940 | 1/1994 | Kissel | 435/6 |
| 5,332,659 | 7/1994 | Kidwell | 435/6 |

OTHER PUBLICATIONS

Kitamura, Nuclei Acid Research (1991) 67–68.
Jiang et al Huaxue Xuebao (1991) 149:854.

*Primary Examiner*—W. Gary Jones
*Assistant Examiner*—Carla Myers
*Attorney, Agent, or Firm*—Thomas E. McDonnell; Barry A. Edelberg

[57] ABSTRACT

The fluorescence of polycyclic aromatic labels, and excimers of these labels, attached to nucleic acids is greatly enhanced by the presence of quaternary ammonium surfactants having at least one long chain (C4 or greater) alkyl group. This enchancement may be advantageously used in Pi Overlapping Rings Systems Contained in a Homogeneous Assay (PORSCHA) and in conventional assays.

18 Claims, 14 Drawing Sheets

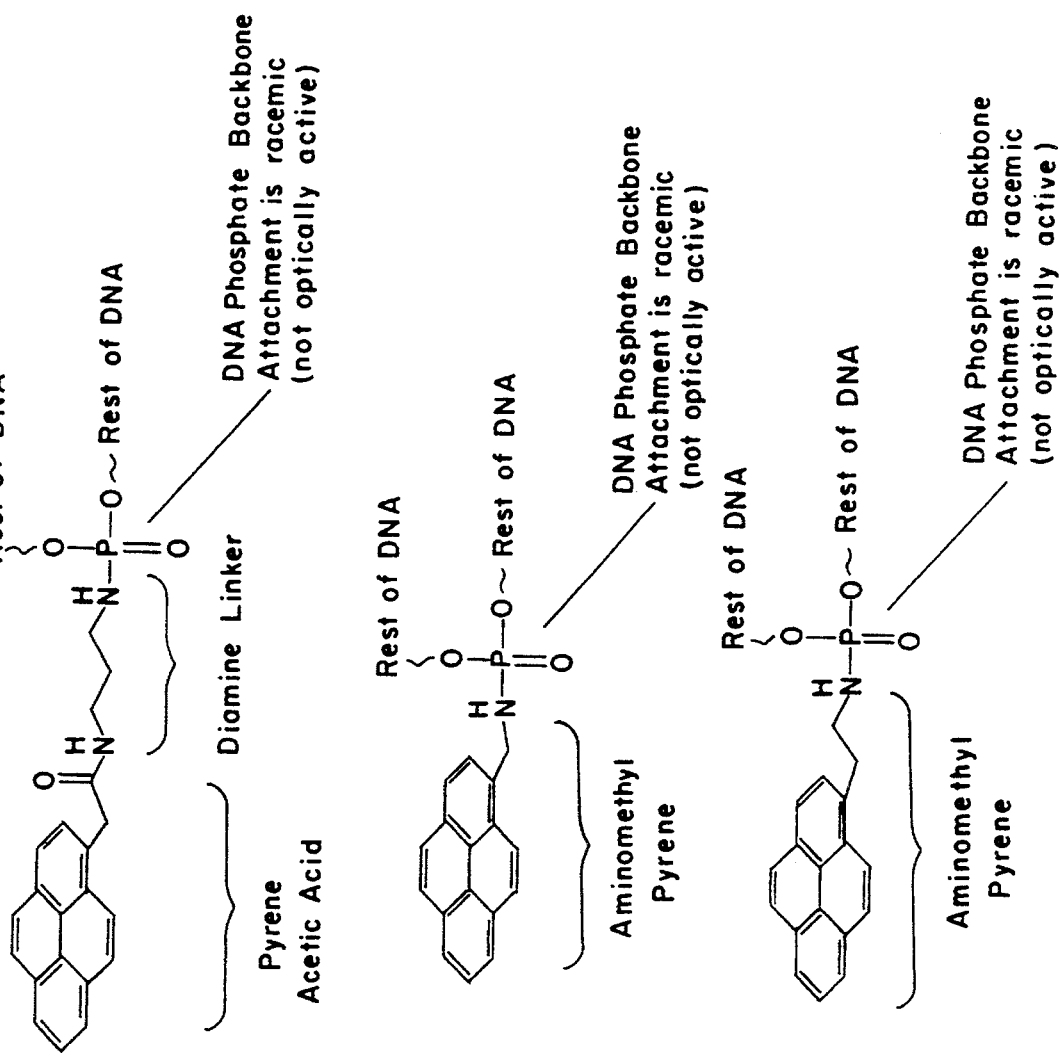
FIG. 12a  M13-3M(PAA-PDA)
FIG. 12b  M13-1MC(PMA)
FIG. 12c  TA-F1A(PEA)

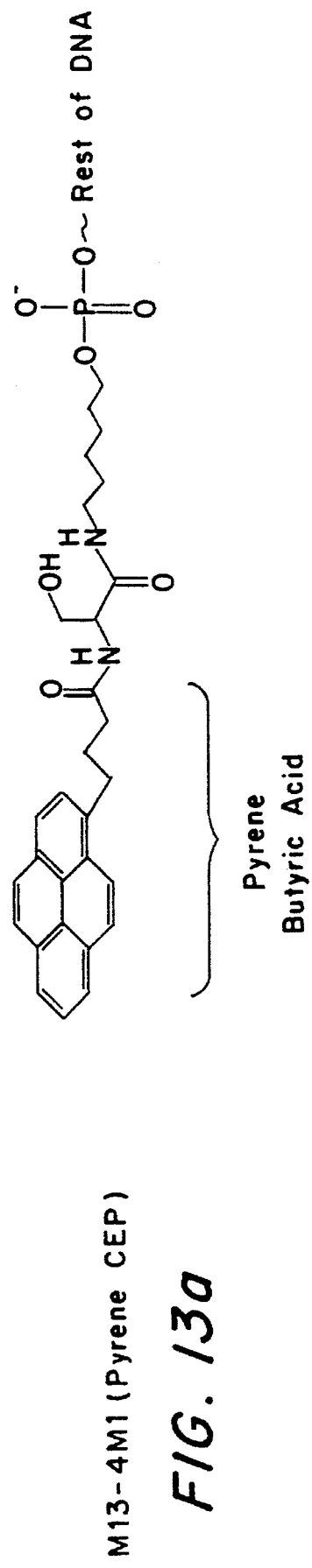
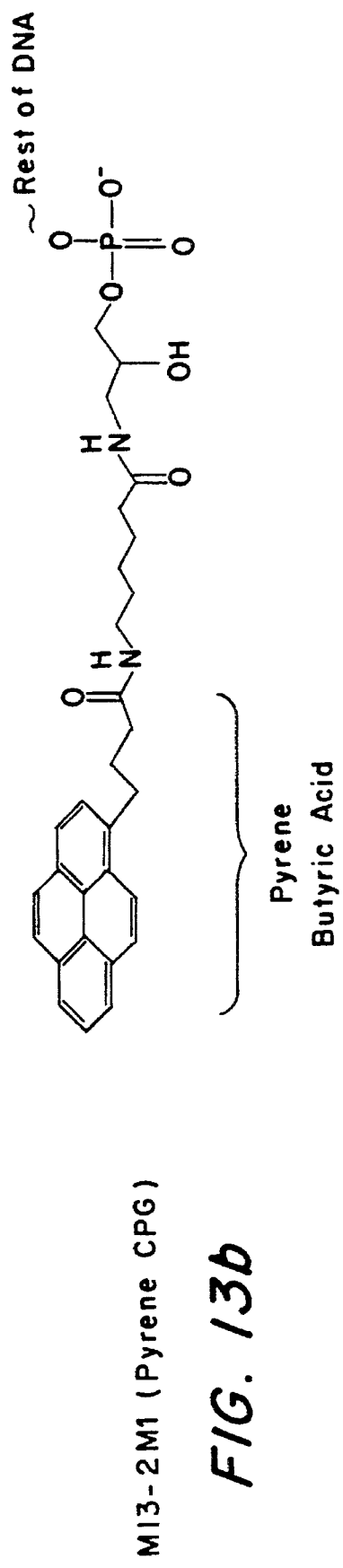
FIG. 13a — M13-4M1 (Pyrene CEP)
FIG. 13b — M13-2M1 (Pyrene CPG)

SURFACTANT-ENHANCED LIGHT EMISSION- OR ABSORBANCE-BASED BINDING ASSAYS FOR POLYNUCLEIC ACIDS

CROSS-REFERENCE TO RELATED APPLICATIONS

This application is a continuation-in-part of David A. Kidwell's Patent application U.S. Ser. No. 08/004,009, filed Jan. 15, 1993, now U.S. Pat. No. 5,332,659 which is a continuation-in-part of U.S. Ser. No. 07/865,526, filed Apr. 9, 1992, now U.S. Pat. No. 5,314,802, both of which are incorporated by reference herein in their entireties.

BACKGROUND OF THE INVENTION

1. Field of the Invention

The present invention relates generally to assays and more specifically to light emission- or absorbance-based binding assays.

2. Background Art

Binding assays, for example, immunoassays and receptor based assays, are widely used in the medical community as diagnostic tests. There are several binding assays that have been produced and are currently on the market since the principle was developed by R. S. Yalow and S. A. Berson, J. Clinical Investigations, 39 1157(1960). An example of a binding assay is Radioimmunoassay (RIA) (D. Monroe, Anal. Chem., 56 920A(1984)). All immunoassays exploit the binding capabilities of antibodies. However other molecules that are capable of recognizing and specifically binding other molecules may be employed. Antibodies are protein molecules which are frequently considered fighters of infections. They fight infections by binding to the infectious material in a specific manner, forming a complex. This is then a signal to the organism to reject that complex. However, antibodies may also be produced to bind to an individual compound, as a key fits a lock. To be useful in an assay, this recognition event must generate a signal that is macroscopically observable. The method employed to generate such a signal is what distinguishes the various types of immunoassays. In the above example, radioactivity is employed. RIA is quite sensitive and widely used, but the expense and restrictions for handling radioactive material makes alternative immunoassays desirable.

Fluorescence and chemiluminescence have been used in various types of assays, such as enzyme assays and immunoassays. In each of these systems, energy-coupling reactions have been exploited.

Carmel et al., FEBS Letters, Vol. 30, No. 1, February 1973, pages 11 through 14, describe the use of fluorescent donors and acceptors which are in close proximity to each other to measure the rate of enzymatic cleavage of a suitable labeled peptide. In their system, a peptide is labeled with two fluorophores. One fluorophore (the donor) accepts excitation light and fluoresces. If the other fluorophore (the acceptor) is in close proximity to the donor, it can accept the emitted light of the donor as excitation light or energy and then emit its own fluorescence. Since Förster, Ann. Physik., 2 55(1948), has shown that the probability of the donor exciting the acceptor decreases with the sixth power of the distance between them, if they are separated by enzymatic cleavage of the peptide linker, the fluorescence of the acceptor will decrease substantially. Thus, a measure of the fluorescent intensity of the acceptor is inversely proportional to the rate of enzymatic activity. Although such a system is quite sensitive, it is difficult to find appropriate donors and acceptors such that the donor may be exclusively excited by the incident radiation without exciting the acceptor.

Binding assays have been produced by using the donor/acceptor scheme described above. In this case, the donor is a fluorescently labeled hapten and the acceptor is the antibody with many fluorescent acceptors attached. This large concentration of fluorescent acceptors is needed because the distances are greater than in simple peptide enzymatic substrates. However, the same problems occur with finding appropriate donors and acceptors that occur with enzymatic substrates. Patel et al., Clin. Chem., Vol. 29, No. 9, 1983, 1604–1608, have overcome some of these difficulties by using chemiluminescence to excite the donor. To achieve the reported high sensitivities, a very sensitive instrument must be employed.

Similar systems (Pohl et al., Analytical Biochemistry 165, 96–101 (1987)) have used fluorescent quenching to measure the distance between a quencher and a fluorophore, both attached to the same peptide linker. The increase in fluorescence when the peptide linker is cleaved is a measure of the enzymatic activity. However, the quencher is not very efficient in reducing fluorescent such that only a five- to eight-fold increase in fluorescence is observed when the peptide linker is cleaved.

Polynucleic acids, such as DNA, RNA, and DNA-RNA complexes form a double helix in solution by recognizing and binding to its complementary strand. This recognition feature can be used to detect organisms and viruses in the environment and to identify nucleic, as in DNA fingerprinting. Polynucleic acid-polynucleic acid recognition is analogous to antibody-antigen recognition. To perform most polynucleic acid assays, a labeled form of polynucleic acid is added to the matrix, allowed to bind its complementary strand, and the double-stranded, helical polynucleic acid separated from the unbound polynucleic acid. Then the label is detected by some means, as described, for example, in J. I. Thornton, Chemical Engineering and News, Nov. 20, 1989, pp 18–30. Many of these detection schemes require extensive and laborious procedures to separate the bound, helical polynucleic acid from the unbound polynucleic acid so that detection of the label and hence the complementary strand of polynucleic acid can be made.

SUMMARY OF THE INVENTION

Accordingly, it is an object of this invention to provide a binding assay where no separation steps are necessary for measurement.

It is another object of the present invention to provide an amplification scheme which is not subject to decrease in activity over time in storage, as are assays using radioactivity or enzymes.

It is a further object of the present invention to replace radioactivity with an environmentally safer detection scheme, yet, at least in some embodiments, maintain the sensitivity that radioactivity permits.

It is yet another object of the present invention to detect the presence of a specific polynucleic acid without requiring the separation of the polynucleic acid bound to a complementary strand from the polynucleic acid which is not bound to a complementary strand.

These and additional objects of the invention are accomplished by replacing radioactivity with a fluorescent molecule, such as pyrene, which shows a change in spectra with concentration.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein:

FIGS. 12a, 12b and 12c show the structure and code names of linkers used in some examples of nucleic acid detection according to the present invention.

FIGS. 13a and 13b show the structure and code names of additional linkers used in some examples of nucleic acid detection according to the method of the present invention.

DETAILED DESCRIPTION OF THE PREFERRED EMBODIMENT

Figure 1A:
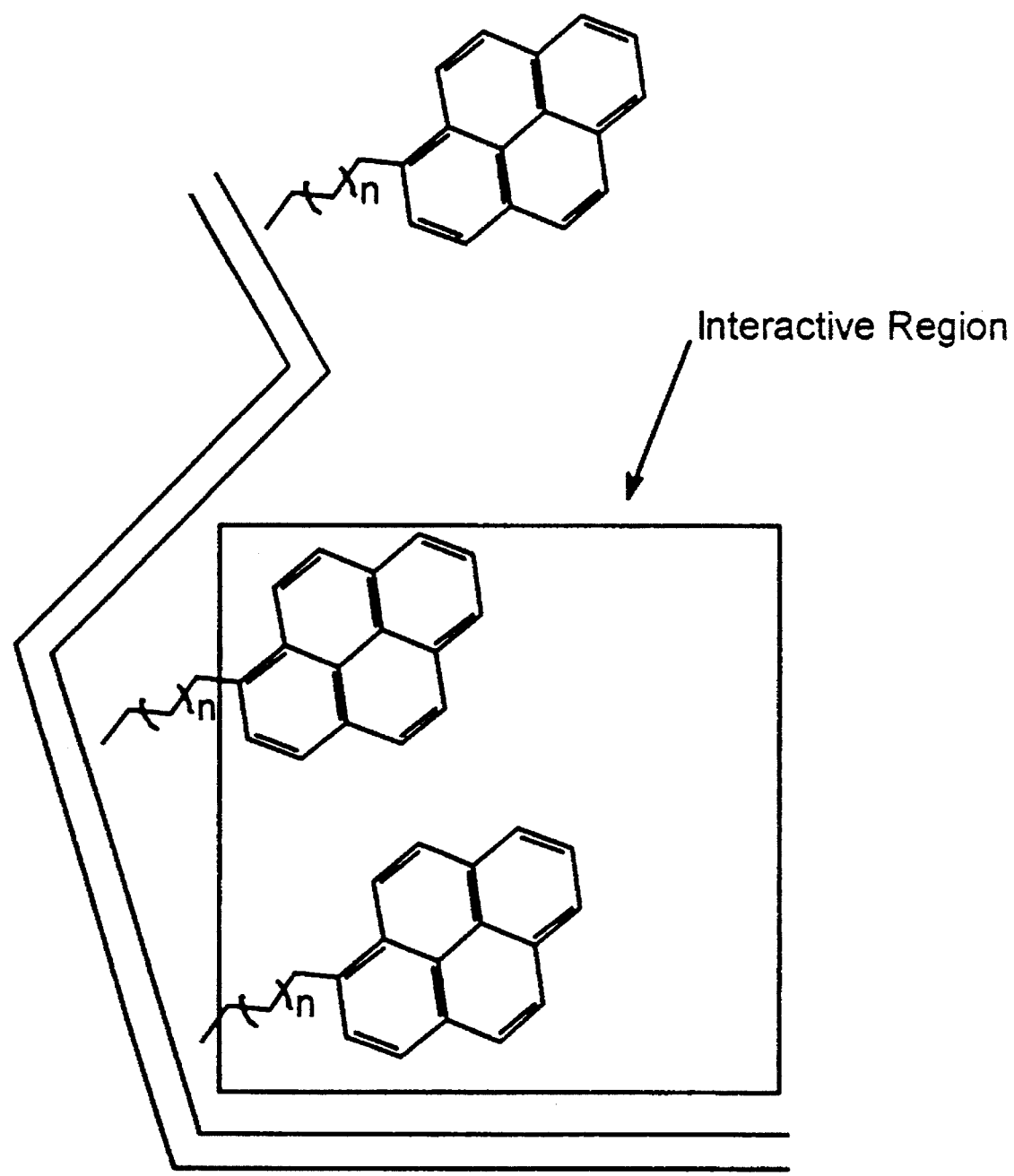
FIGS. 1a and 1b show schematically the use of PORSCHA for the detection of polynucleic acid binding.

In the present disclosure and claims, binding assays are defined as assays using molecules, molecular complexes or surfaces that selectively bind two or more other molecules. This definition encompasses but is not limited to antibodies, antibody fragments, streptavidin, avidin, receptors, lectins, surfaces and polynucleotides such as DNA, RNA, and DNA-RNA complexes.

The method according to the present invention relies on a label which varies the wavelength dependance of its spectra (either emission, transmission, or absorbance) depending upon its concentration. An example of such a molecule is pyrene and its derivatives.

Pyrene possesses different fluorescent spectra at high and low concentrations. At high concentrations two pyrene molecules are close enough for the pi-systems to overlap. It is well-known that the interaction of the pi systems causes emission of light having an emission maximum at a longer wavelength (~480 nm). At low concentrations the pyrene molecules are too far apart for two pyrene molecules to interact and only an emission at 378 and 396 nm is observed. Thus, the ratio of light emitted at 378 and 396 nm to 480 nm is a measure of the concentration of pyrene in the sample.

Pyrene and closely related pyrene derivatives (structures containing the four-membered ring system characteristic of pyrene) are the best choices for indicators according to the present invention because they show strong differences in fluorescent spectra with concentration and have long fluorescent lifetimes if time-resolved spectroscopy is used to resolve background interferences. Other compounds which show similar change spectral absorption or emission maxima dependant upon concentration may also be used. In general, polycyclic aromatic compounds, such as napthalene, perylene, and various fluorescent dyes, such as acridine orange, or BODIPY® (a boron-containing fluorescent dye), a trademarked product of Molecular Probes, Inc., and its derivatives, may be used as labels according to the present invention.

The spectral change can be observed by various means. For example, the emission spectra of the label can be measured after excitation with any form of energy, such as electromagnetic radiation, heat, particle radiation, or chemical energy (chemiluminescence). Alternatively, the spectral absorbance of the label can be monitored, although decreased sensitivity would be expected.

The linker is preferably flexible. Examples include, but are not limited to, polyethylene oxides, alkyl chains, polyamino acids, polyamides. The only requirements are matrix-solubility at the concentration used and appropriate length.

In performing an assay according to the present invention, a buffer is needed to both dilute the components and provide an environment in which the binding of the tracer can occur. Many types of buffers may be employed, including those containing protective proteins, such as bovine serum albumin, gelatin and casein, or protective DNA.

The assay according to the present invention can be performed in aqueous or non-aqueous media. Typically, the matrix within which bioassays according to the present invention is performed is aqueous-based. However, molecules such as antibodies have been shown by others to selectively bind other molecules in substantially non-aqueous media, such as air.

In the detection of polynucleic acids by PORSCHA (Pi Overlapping Rings Systems Contained in a Homogeneous Assay), it is essential that the label be attached to the sensing polynucleic acid strand only, such that, when the labeled polynucleic acid strand binds to an at least substantially complementary polynucleic acid strand (i.e., a polynucleic acid strand capable of hybridizing with the labeled polynucleic acid strand under the assay conditions), the label is attached to the exterior of the helical chain, i.e., the label should not be intercalated between the two strands of the polynucleic acid helix. Therefore, the labeled polynucleic acid strand should not be labeled at its the amino termini of its bases. Preferably, the label should be attached to the nucleotides at the internucleotide phosphorus atom, or between the phosphorus atoms as shown schematically in FIG. 3.

Figure 1B:
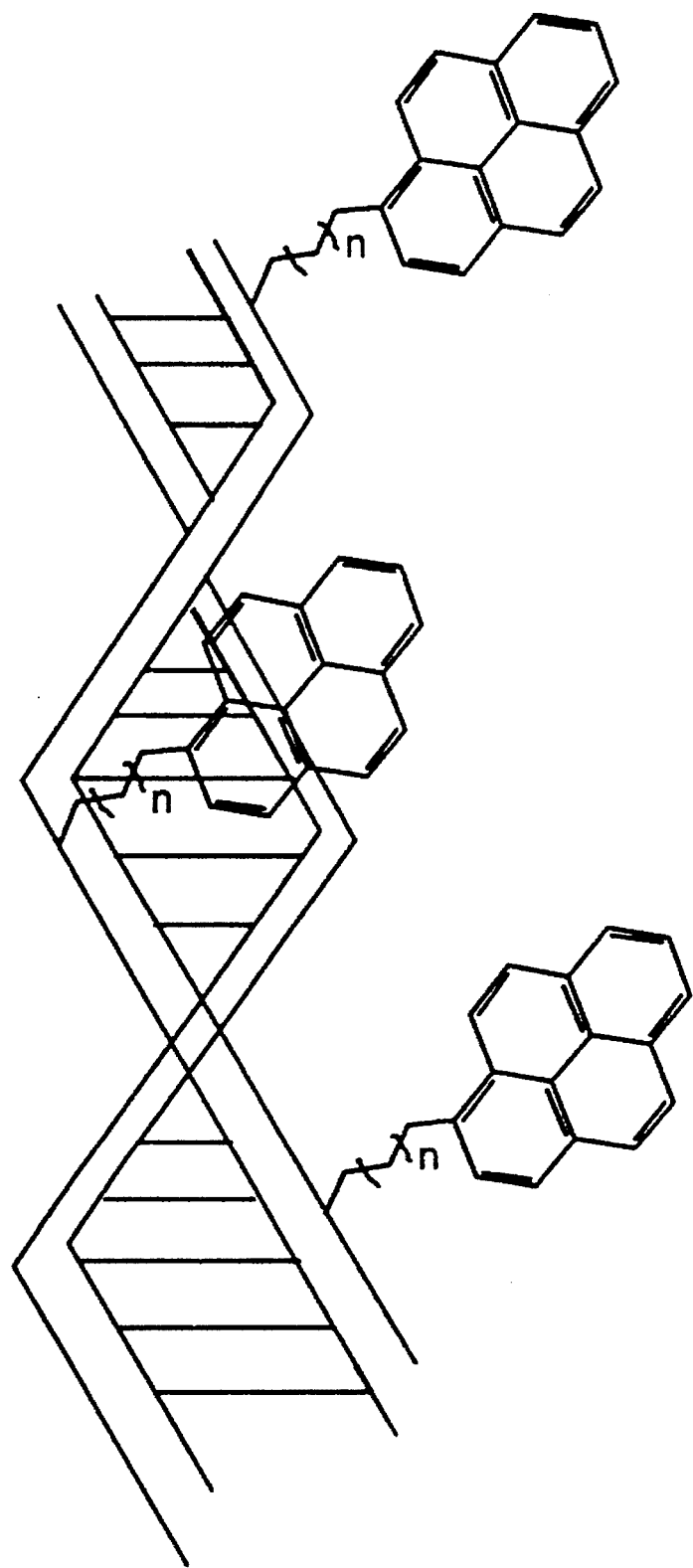

One method by which PORSCHA could be applied to polynucleic acid detection is outlined in FIGS. 1a and 1b. A sensing strand of polynucleic acid (one complementary to the strand of target polynucleic acid being analyzed) is labeled with nucleotides containing labels with fluorophore moieties, for example pyrene molecules. In solution (FIG. 1a), single-stranded polynucleic acid can take many forms; it has many degrees of freedom. Thus, there is a good probability that two fluorophore moieties could come close enough together to overlap and electronically interact to alter their spectral emission or absorption, for example, by forming a complex such as an excimer. Also, a fluorophore moiety such as a pyrene ring system would be constrained to remain together due to the strong interactions of two pyrene pi systems of about 18 kcal/mol. Therefore, the single stranded polynucleic acid should show a spectral change. When this labeled form of double-stranded polynucleic acid binds to its complementary strand forming a double helix (FIG. 1b), the freedom of motion is greatly constrained. The distance between the labeled phosphates along the labeled polynucleic acid strand is selected such that, in the double helical form, the fluorophore moieties would be pulled apart. Because the motion of the fluorophore moieties would be greatly constrained in the double helical polynucleic acid, they could not interact and hence no electronic interaction would be present. Thus, the absence of, or a decrease of, a variation in the emission or absorbance spectra would indicate the presence of the target polynucleic acid.

In another method for applying PORSCHA to polynucleic acid detection, the strand of polynucleic acid complementary to the target polynucleic acid strand may be labeled in such a manner that the distance between the labeled phosphate groups is small. In this embodiment, the length of the linker arm between the phosphate group and the fluorophore moiety of the label should be selected to reduce the freedom of motion of the fluorophore moieties, thus minimizing the electronic interaction of fluorophore moieties of the single-stranded polynucleic acid sensing strand in solution. When the target polynucleic acid strand is added to the solution, the sensing strands binds to it and forms a double helix, thus positioning the fluorophore moieties sufficiently close to each other to electronically interact and form and alter their spectral absorption or emission, for example, by forming a complex such as an excimer.

Figure 2:
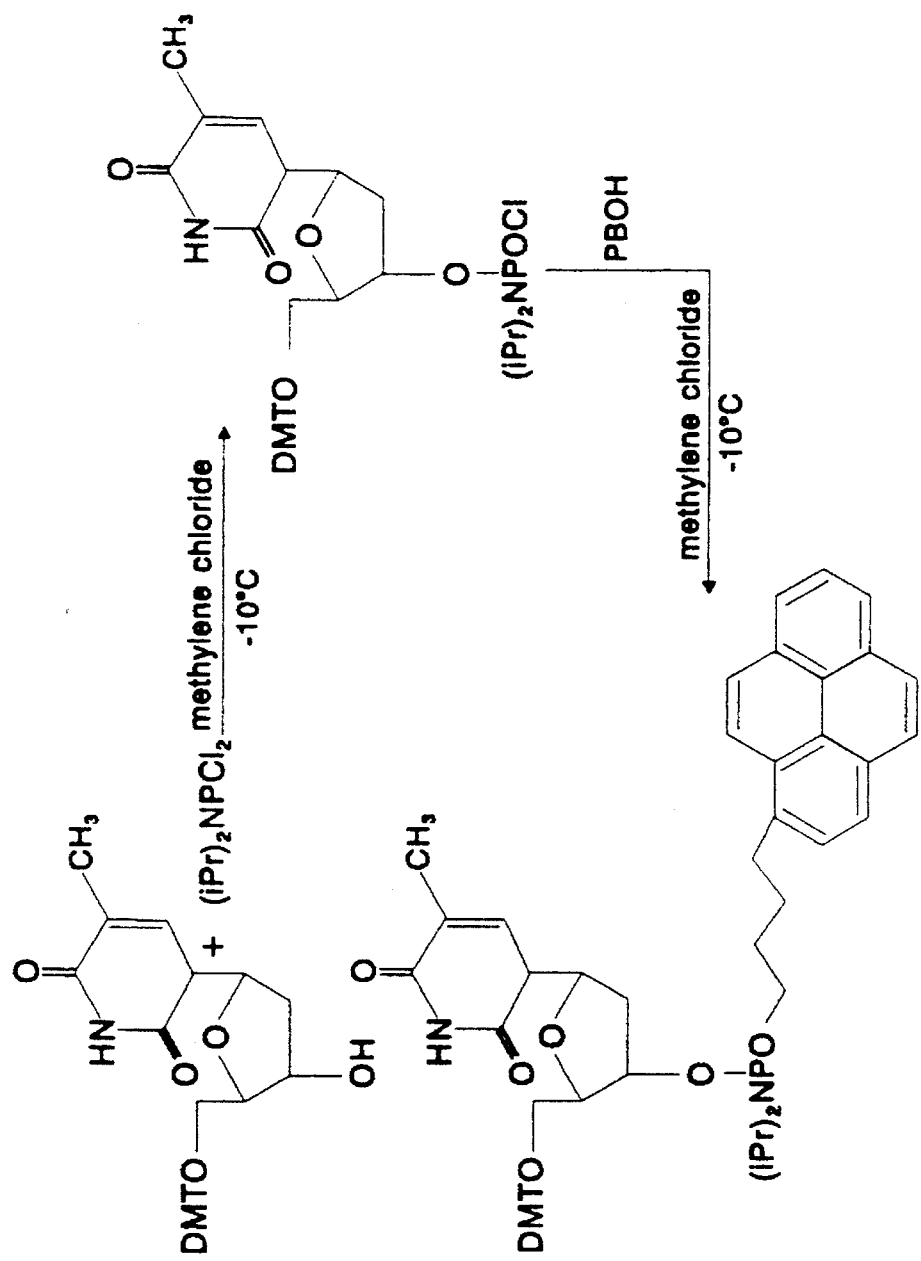
FIG. 2 schematically illustrate the preparation of a labeled DNA base for use in automated DNA synthesizers. In this figure, "DMT" is dimethoxytrityl and "iPr" is isopropyl.

In discussing polynucleic acid detection using PORSCHA, it is convenient and preferred to define the linker as the moiety between the phosphorus atom and the fluorophore moiety of the label. Thus, in FIG. 2, the linker arm is five atoms long.

Of course, some complex formation may always be present in each embodiment useful for polynucleic acid detection, whether the target polynucleic acid strand is present or absent. Accordingly, a significant change in the intensity of the variation in the absorption or emission spectra of the complex would indicate, depending upon the embodiment, the presence or absence of the target polynucleic acid strand. Whether an intensity change is significant will of course depend upon the instrumentation selected, the amount of target polynucleic acid present in the matrix, the label selected, and the precision and error level which the person performing the test considers acceptable.

One advantage of PORSCHA as applied to polynucleic acid detection, is that no separation step need be preformed to determine if the target polynucleic acid is present. Also, a tracer DNA oligomer may be integrated with PCR, as one of the PCR primers, or as independent probe to the DNA being synthesized (preferably 3'-blocked), and the change in complex/monomer ratio monitored with time as the PCR progresses. Such a system offers both the amplification advantage of PCR coupled with the monitoring of the reaction with time. Thus if the signal increases very rapidly as the PCR progresses, a large amount of target polynucleic acid would be indicated. If the signal does not change or changes only slowly, no target polynucleic acid or less target polynucleic acid would be indicated. Analogous amplification can be performed on polynucleic acids other than DNA, as is well-known in the art. A homogeneous assay for polynucleic acid coupled to PCR could be a valuable technique for the diagnosis of bacterial or viral infections.

Pyrene has many useful qualities as a fluorescent label. It is photochemically and chemically stable and has a long fluorescent lifetime that is useful in reducing background fluorescence in complex matrices by fluorescence lifetime measurements (for example see: Morrison, Analytical Biochemistry 174 101–120 (1988)). In most systems, pyrene is resistant to fluorescent quenching. However, when nucleic acids are labeled with pyrene, the fluorescence intensity of pyrene is significantly reduced compared to the same concentration of pyrene in solution. For example: Morrison, et al., (Analytical Biochemistry 183 231–244(1989)) observed that with 3' pyrene butyrate labeled oligomers the fluorescent quantum yield of the pyrene label was 100-fold less than that of unconjugated pyrene. Telser, et al., (J. American Chemical Society 111 6966–6976(1989)) studied DNA oligomers containing a thymidine base labeled with pyrene through a short three-carbon linker. They observed a relative quantum yield of 0.02 for the single stranded DNA and 0.002 for the duplex. Yamana, et al., (Nucleosides and Nucleotides 11 383–390 (1992)) studied pyrene labeled uridine with the pyrene label on the 2' hydroxyl group. The relative quantum yield of this derivative was approximate 0.002 (data calculated from Table 2 of that paper) as the single stand. In contrast to Telser, et al., Yamana, et al., observed a significant increase in fluorescent intensity (2–20.4 times) upon formation of the DNA duplex. However, even in their DNA duplex, the relative quantum yield (recalculated relative to unconjugated pyrene methanol) ranged from only 0,004 to 0.06.

Figure 5:
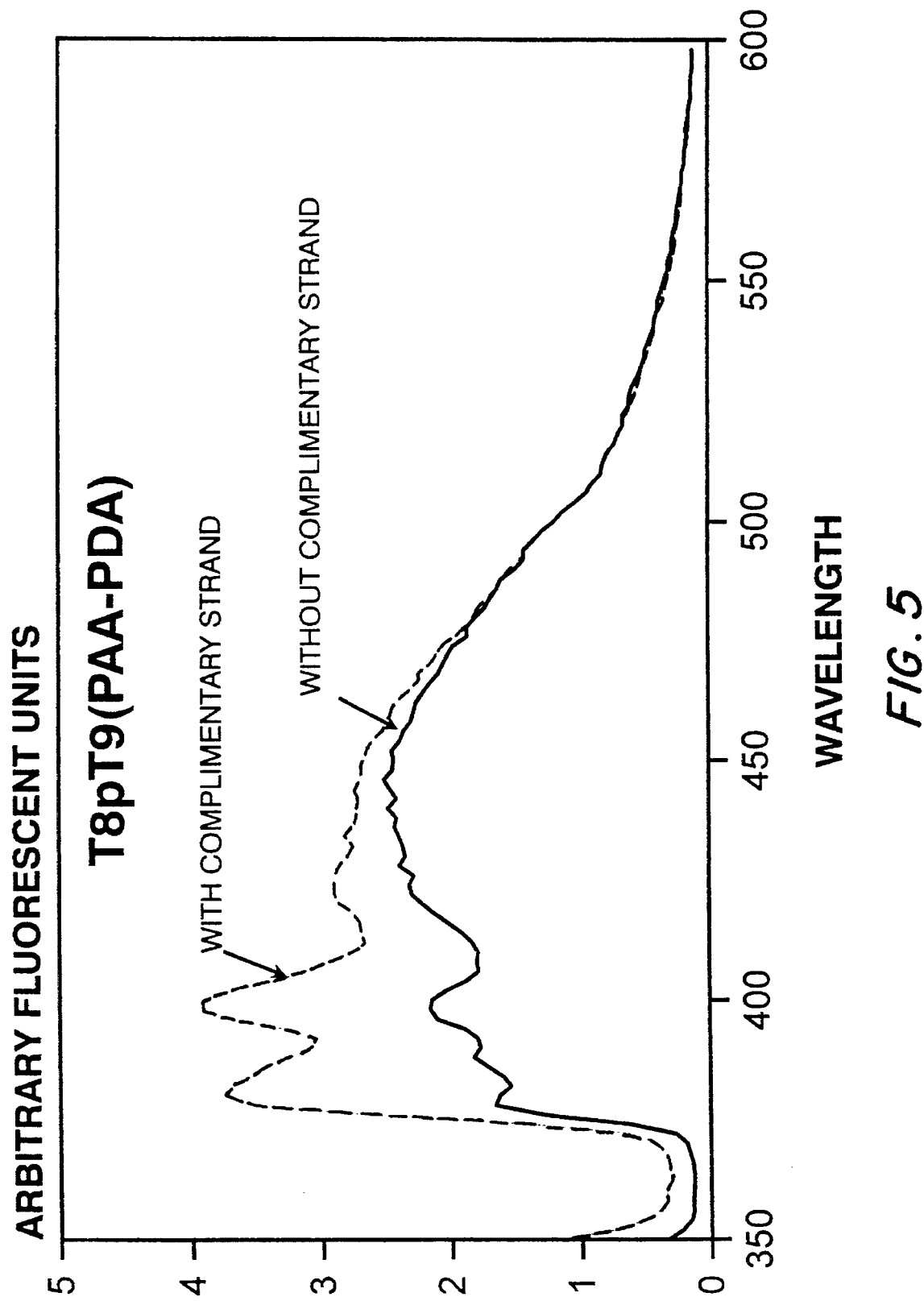
FIG. 5 is a graph that shows the change in fluorescent intensity that occurs upon the addition of an unlabeled complementary strand (in this case RNA) to an appropriately labeled strand of nucleic acid containing one pyrene label.
Figure 6:
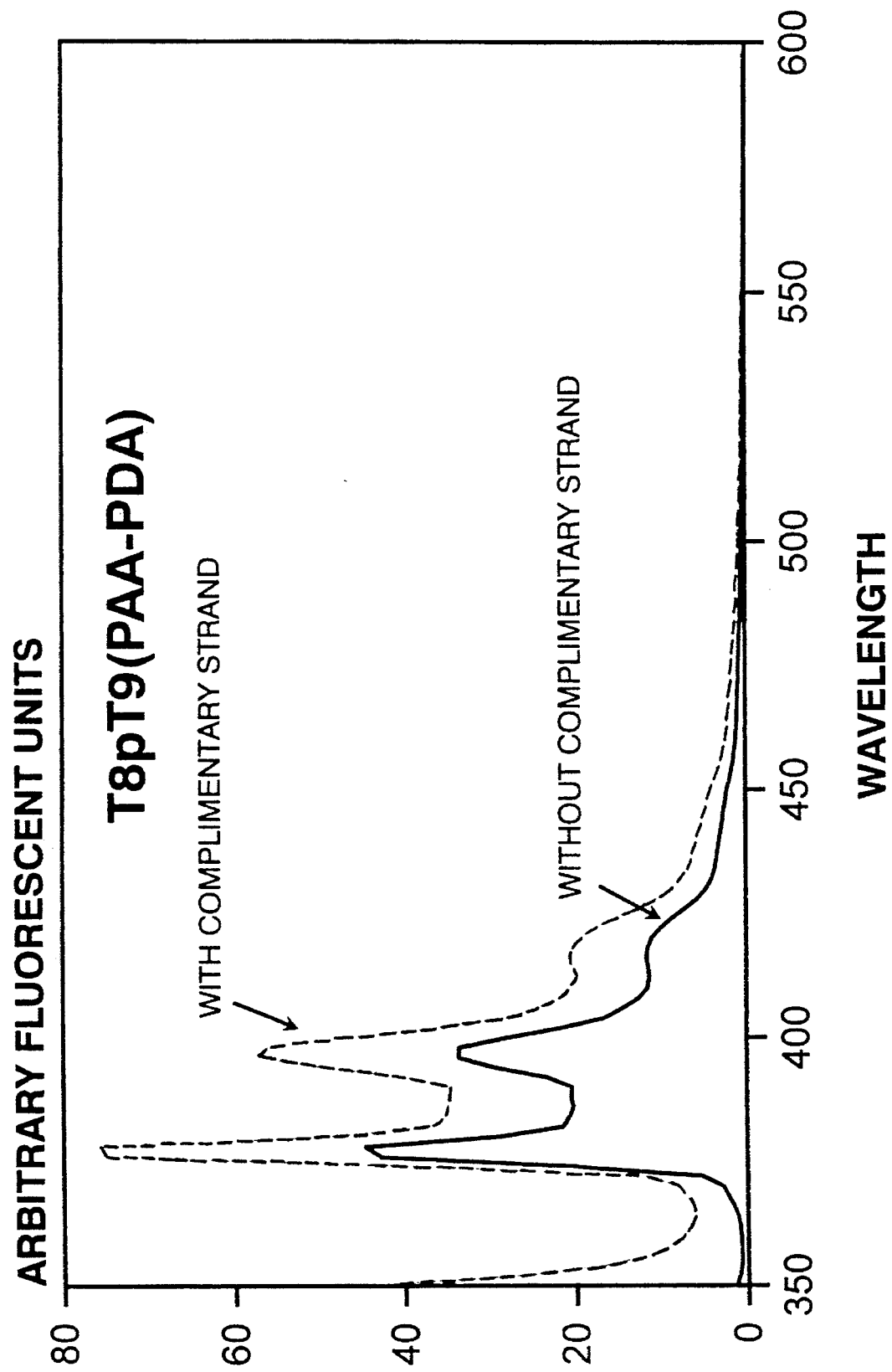
FIG. 6 is another graph showing a change in fluorescent intensity that occurs upon the addition of an unlabeled complementary strand (in this case RNA) to an appropriately labeled strand of nucleic acid containing one pyrene label.
Figure 7:
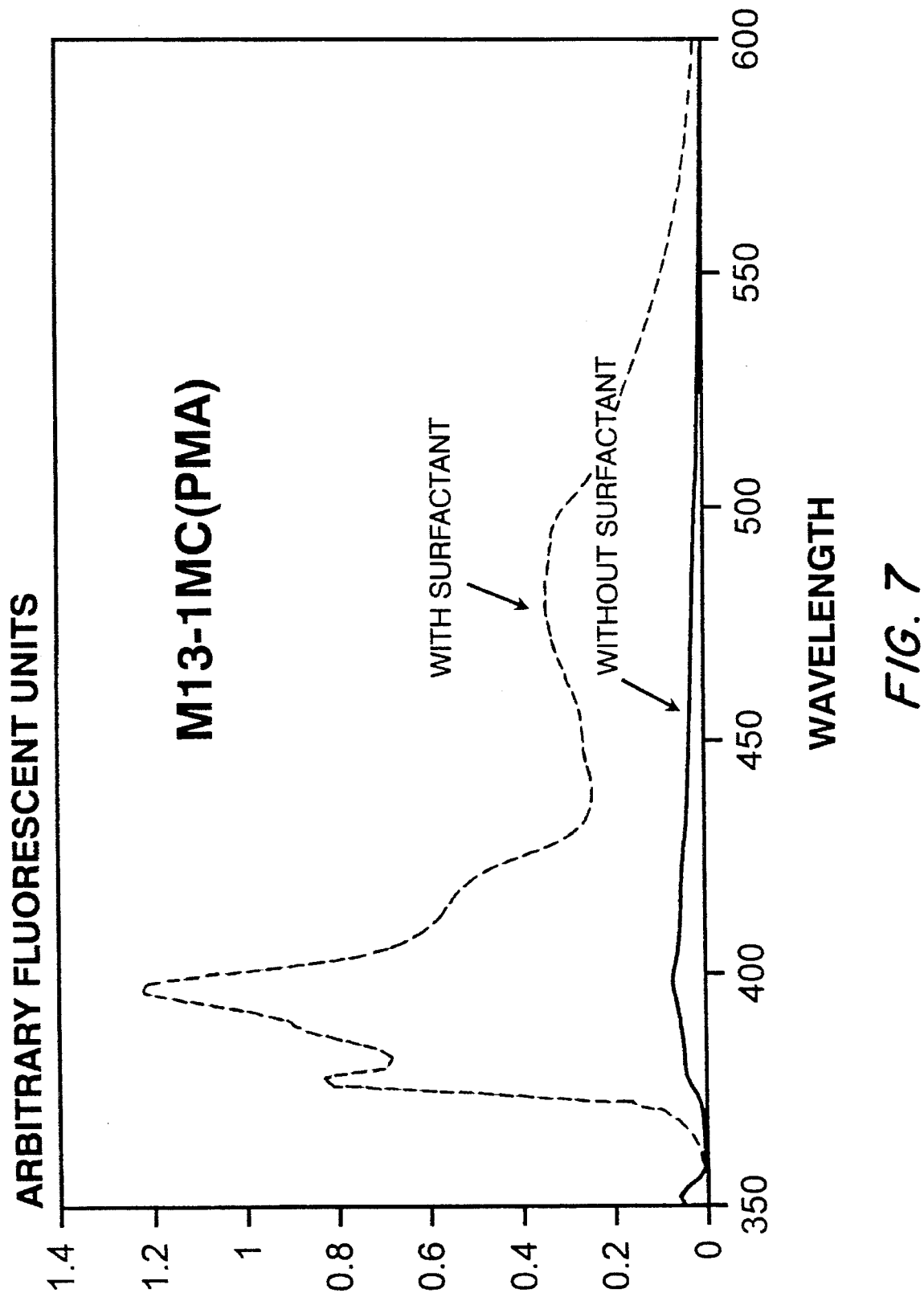
FIG. 7 is a graph showing the change in fluorescent intensity of a nucleic acid strand labeled with two pyrene molecules, with and without the use of hexadecyltrimethylammonium bromide.
Figure 8:
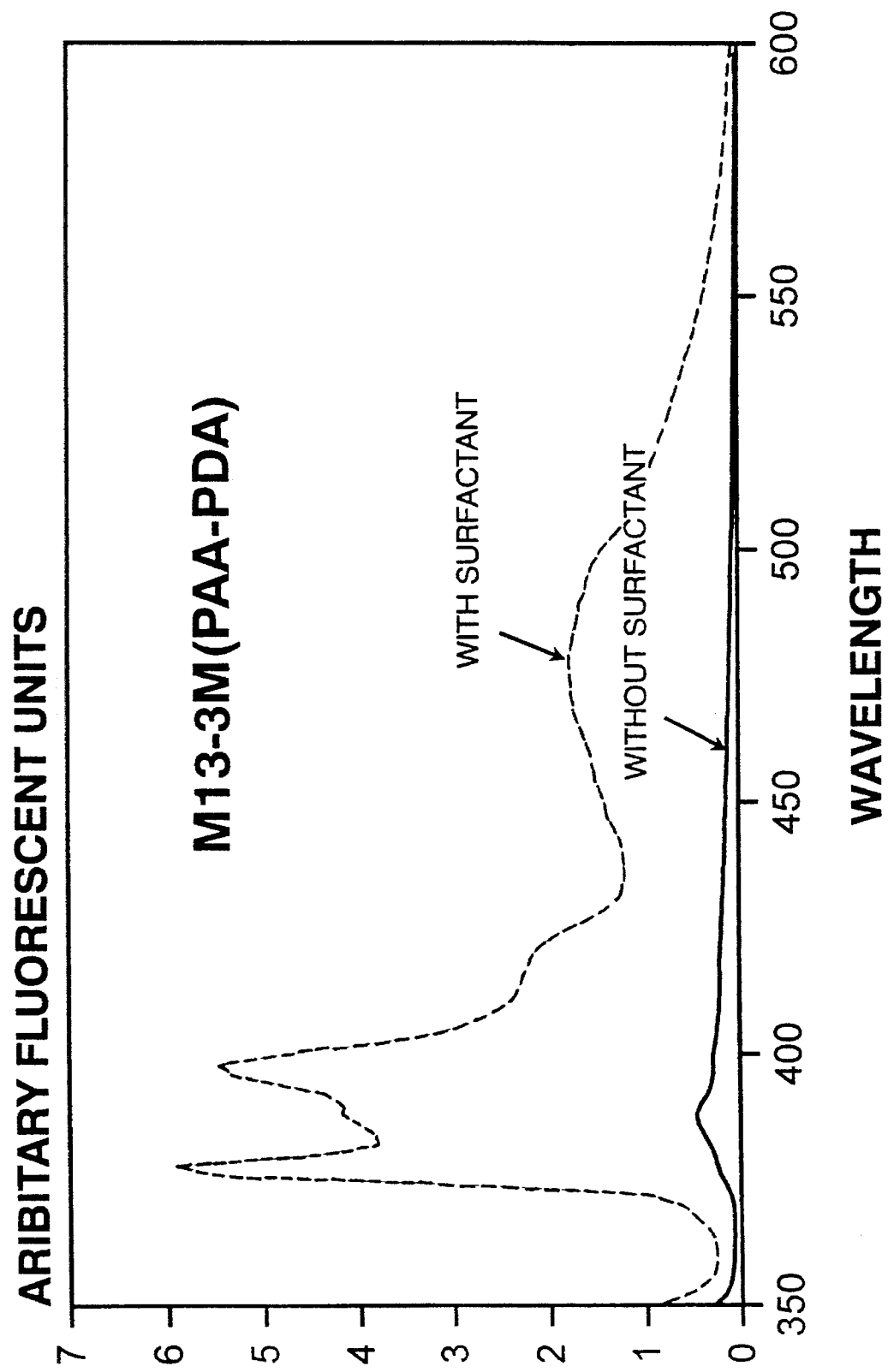
FIG. 8 is another graph showing the change in fluorescent intensity of a nucleic acid strand labeled with two pyrene molecules, with and without the use of hexadecyltrimethylammonium bromide.
Figure 9:
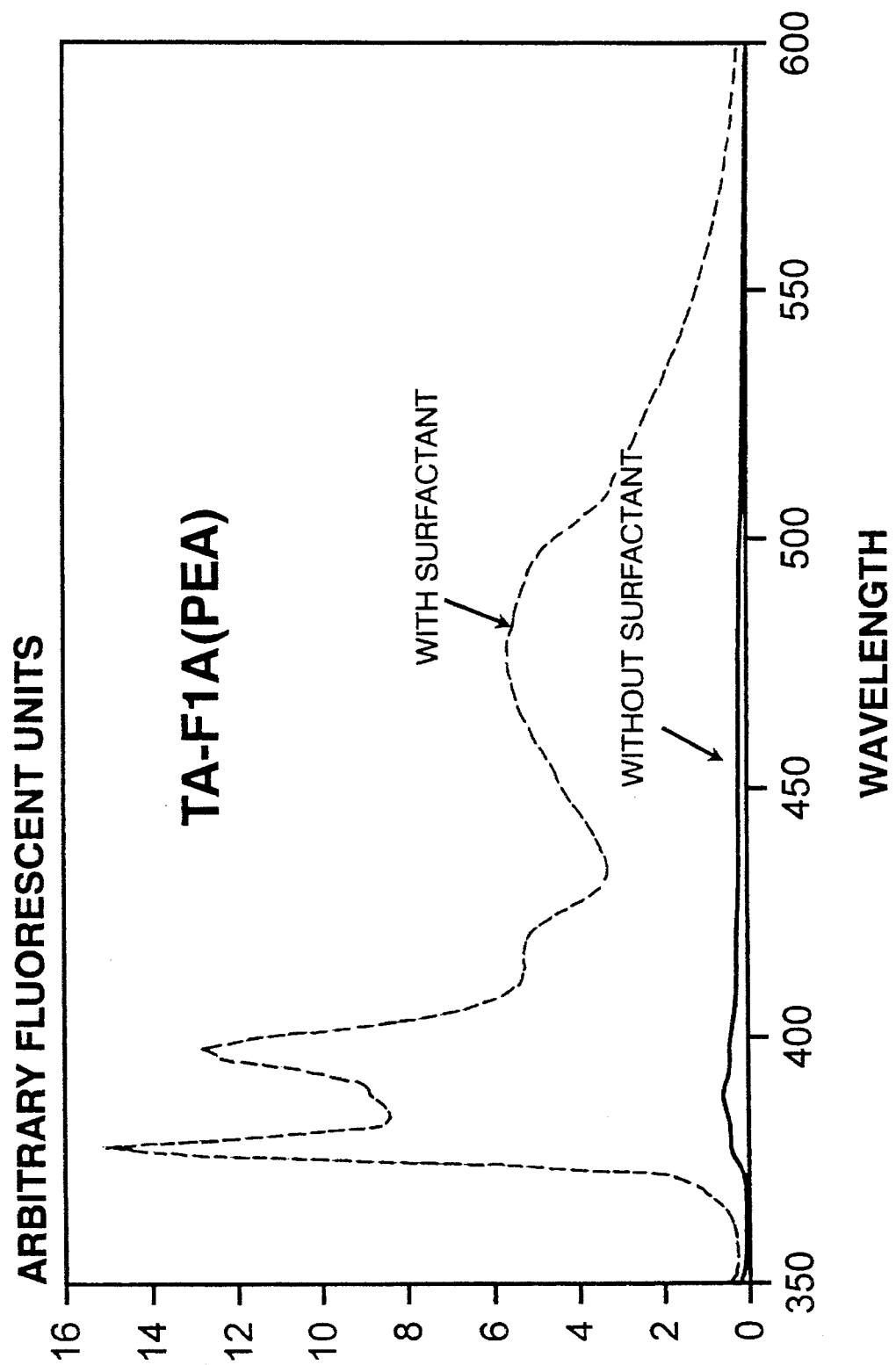
FIG. 9 is yet another graph showing the change in fluorescent intensity of a nucleic acid strand labeled with two pyrene molecules, with and without the use of hexadecyltrimethylammonium bromide.
Figure 10:
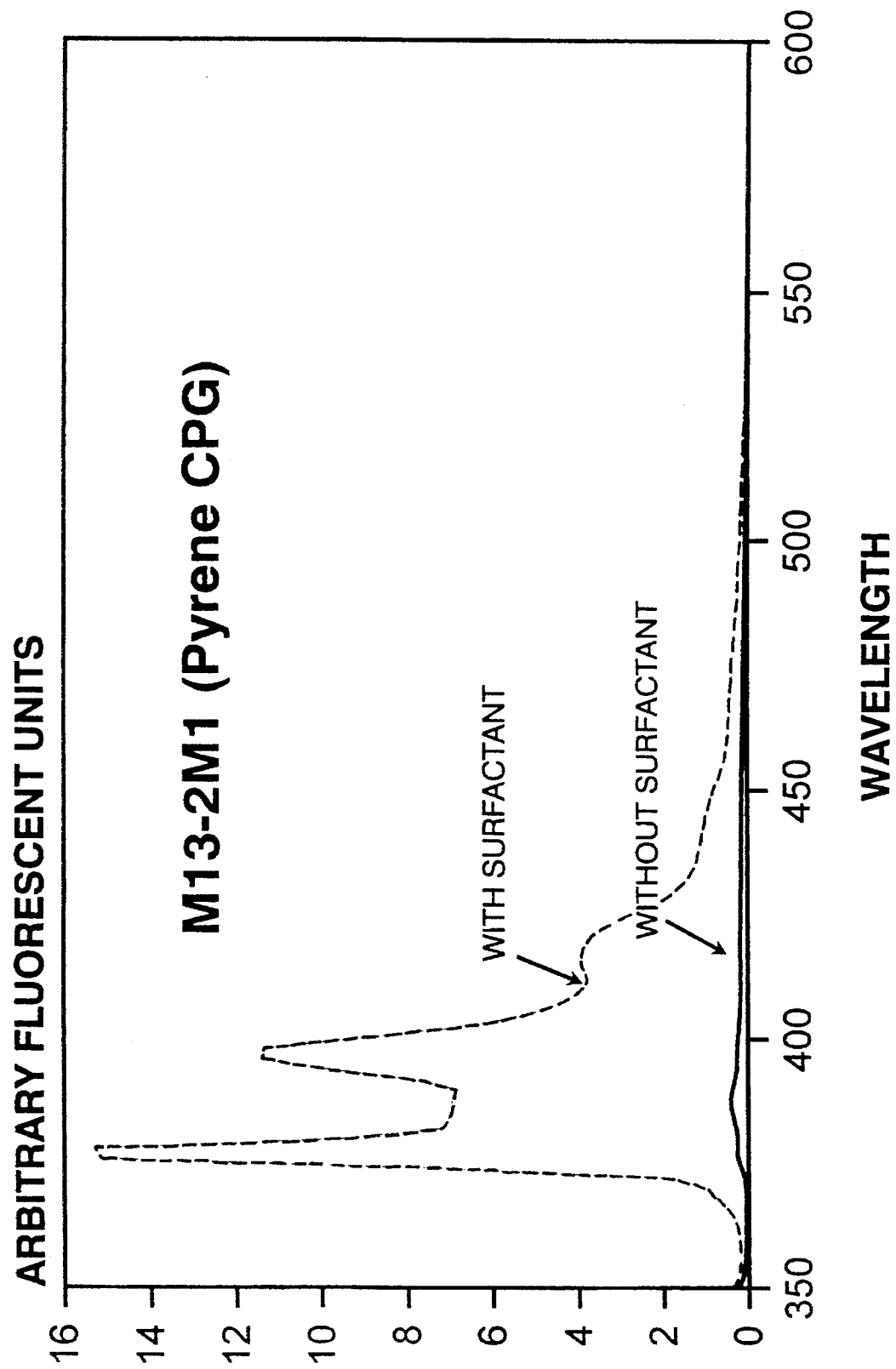
FIG. 10 shows the change in fluorescent intensity of a nucleic acid strand labeled with one pyrene molecule, with and without the use of hexadecyltrimethylammonium bromide.
Figure 11:
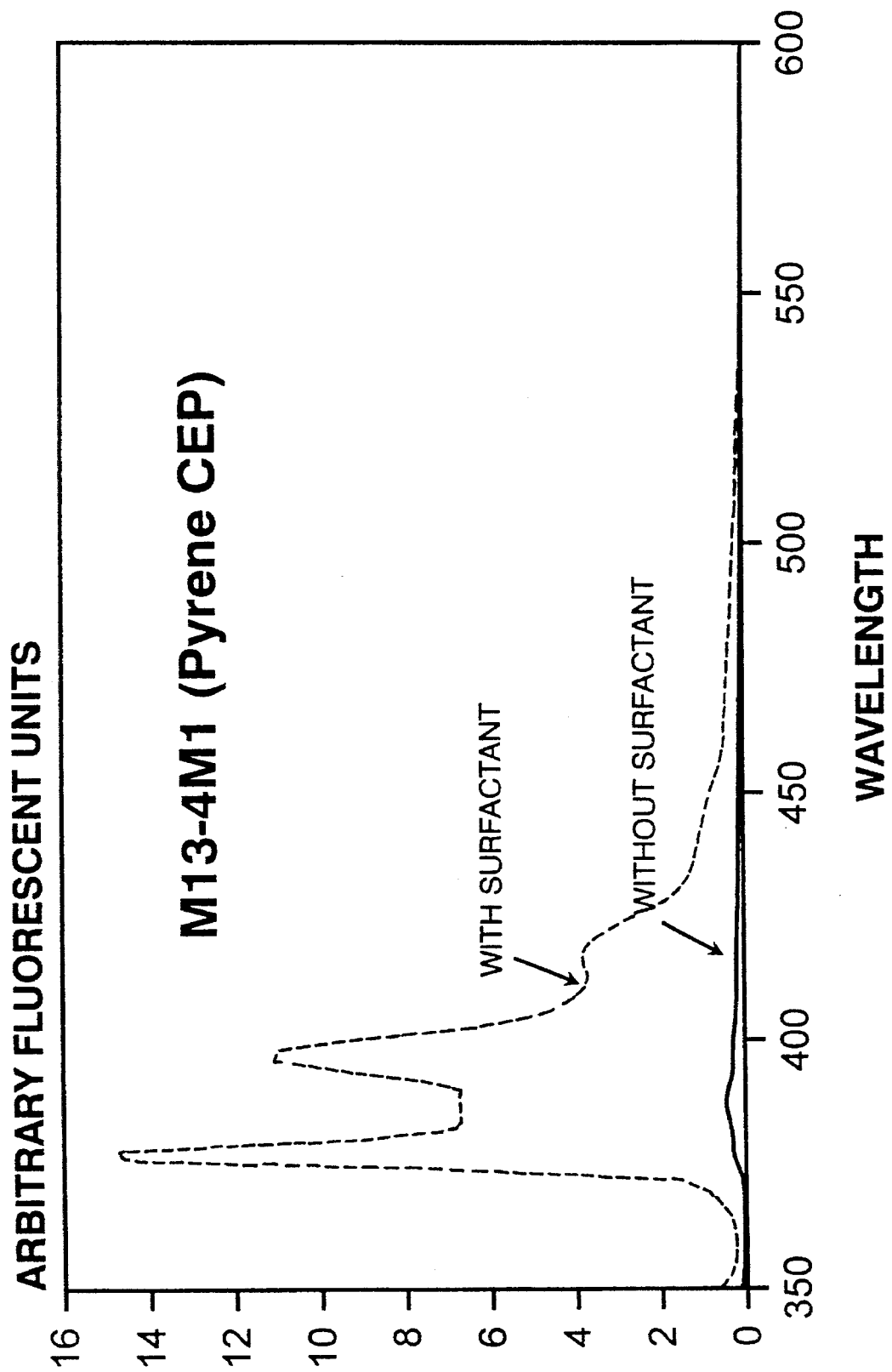
FIGS. 11 also shows the change in fluorescent intensity of a nucleic acid strand labeled with one pyrene molecule, with and without the use of hexadecyltrimethylammonium bromide.

FIG. 5 shows an increase in fluorescence from pyrene labeled oligomers (labeled with only one pyrene label) upon binding to their complementary strand. It has now been discovered that, in the presence of certain surfactants, the fluorescence of polycyclic aromatic compounds such as pyrene is greatly increased in both the single stranded and double stranded form (see FIG. 6).

Only a few surfactants classes cause an increase in pyrene fluorescence. Anionic surfactants such as: sodium dodecyl sulfate, sodium tetradecyl sulfate (Tergitol Anionic 4, Union Carbide), sodium octyl sulfate, and sodium hexadecyl sulfate have little or no effect on fluorescent intensity. Likewise non-ionics such as: Brij 72 (ICI Americas, Inc. Wilmington, Del.), Pluronic 25R2 (BASF Wyandotte Corporation, Wyandotte Mich.), and Pluronic L-61 (Wyandotte) have little effect on the fluorescent intensity. Non-ionics such as Triton X100 (Rhome and Haas, Philadelphia, Pa.) and polyethylenesorbitan monolaurate (Sigma Chemical Co, St. Louis, Mo.) have some effect on the fluorescent intensity, especially of short oligomers such as dTT.

In contrast, cationic surfactants such as hexadecyltrimethyl ammonium bromide (HDTMAB), cetyldimethylethyl ammonium bromide, tetradecyltrimethyl ammonium bromide, decyltrimethyl ammonium bromide, and dodecyltrimethyl ammonium bromide had pronounced effect on the fluorescent intensity. FIGS. 7 through 11 show the 10–100 times fluorescent increase in intensity of pyrene labeled oligomers, labeled in various positions, upon addition of HDTMAB. The increase in intensity is difficult to measure because in the absence of the cationic surfactant, the fluorescence is almost non-existent. The emission spectra is often dominated by Raman scattering from the water and impurity fluorescence. Generally, the greatest increase in intensity has been observed when the cationic surfactant is a long chain (for example, C4 or more, typically at least C8, more often at least C10) quaternary ammonium salts.

Not all cationic surfactants enhance the fluorescence intensity of pyrene labeled oligonucleotides. Some cationic surfactants, such as cetyl pyridinium bromide and lauryl pyridinium bromide do not show this increase in fluorescence intensity, possibly due to absorption of the excitation energy by the pyridinium functionality.

The intensity increase in fluorescence is possibly related to the critical micelle concentration (CMC) of the surfactant. For a homologous series of surfactants decyl-, dodecyl-, tetradecyl-, and hexadecyl- trimethylammonium salts, less surfactant is necessary, the longer the alkyl chain. Therefore, more preferably, HDTMAB is used because of the lower critical micelle concentration for this cationic surfactant. In water, HDTMAB has a CMC of $2.6 \times 10^-$ Molar. The CMC of HDTMAB would be lowered in the typical buffer solutions used for DNA binding but the exact value was not been measured. At the concentrations used in the present invention, the surfactant is likely to be below the CMC. The concentration of the surfactant is not critical and going above the CMC has little effect on the fluorescent intensity of the pyrene reporter probe.

However, it is important to keep the cationic surfactant at as low a concentration as possible because high concentrations are known to precipitate nucleic acids (see: Jones, Biochimica et Biophysica Acta, 10 607–612 (1953), Macfarlane and Dahle, Nature 362 186–188 (1993), and Macfarlane, U.S. Pat. No. 5,010,183). At the concentrations (approximately $1 \times 10^{-5} - 1 \times 10^{-6}$ Molar for HDTMAB) used in the present invention, little or no precipitation of nucleic acids was observed. At higher concentrations of surfactant or with large amounts of nucleic acids, precipitation has been observed. At concentrations greater than $1 \times 10^{-6}$ Molar for HDTMAB little fluorescence increase is observed so that working at higher concentrations is not necessary.

Surfactant-like properties imparted by a long alkyl chain are necessary to observe the increased fluorescence of the pyrene label. Small, non-surfactant, quaternary ammonium salts, such as tetramethylammonium bromide and tetrapropylammonium bromide do not enhance the fluorescence of the pyrene label.

As demonstrated in FIGS. 7 through 11, the increase in fluorescence intensity is independent of the position of the label and the linker to the DNA strand. Various homopolymers of DNA have also been labeled to determine if the quenching of pyrene is dependent on the base near the pyrene label. Both polythymidine, polydeoxyadenosine, and polydeoxycytidine labeled with pyrene on the phosphate groups show similar, significant quenching of the pyrene fluorescence. In all cases, the fluorescence is increased in the presence of the cationic surfactant.

This surfactant-induced increase in fluorescence can be advantageously used in both the method detecting nucleic acids in which only one strand (the sensing strand) is labeled, and in older methods (for example, that disclosed in Telser et al., discussed supra) in which both stands are labeled. The presence of an amount of surfactant effective to significantly enhance the observed fluorescence will enhance the efficacy of either assay.

Having described the invention, the following examples are given to illustrate specific applications of the invention including the best mode now known to perform the invention. These specific examples are not intended to limit the scope of the invention described in this application.

EXAMPLES

Example I—DNA detection by PORSCHA

Figure 3:
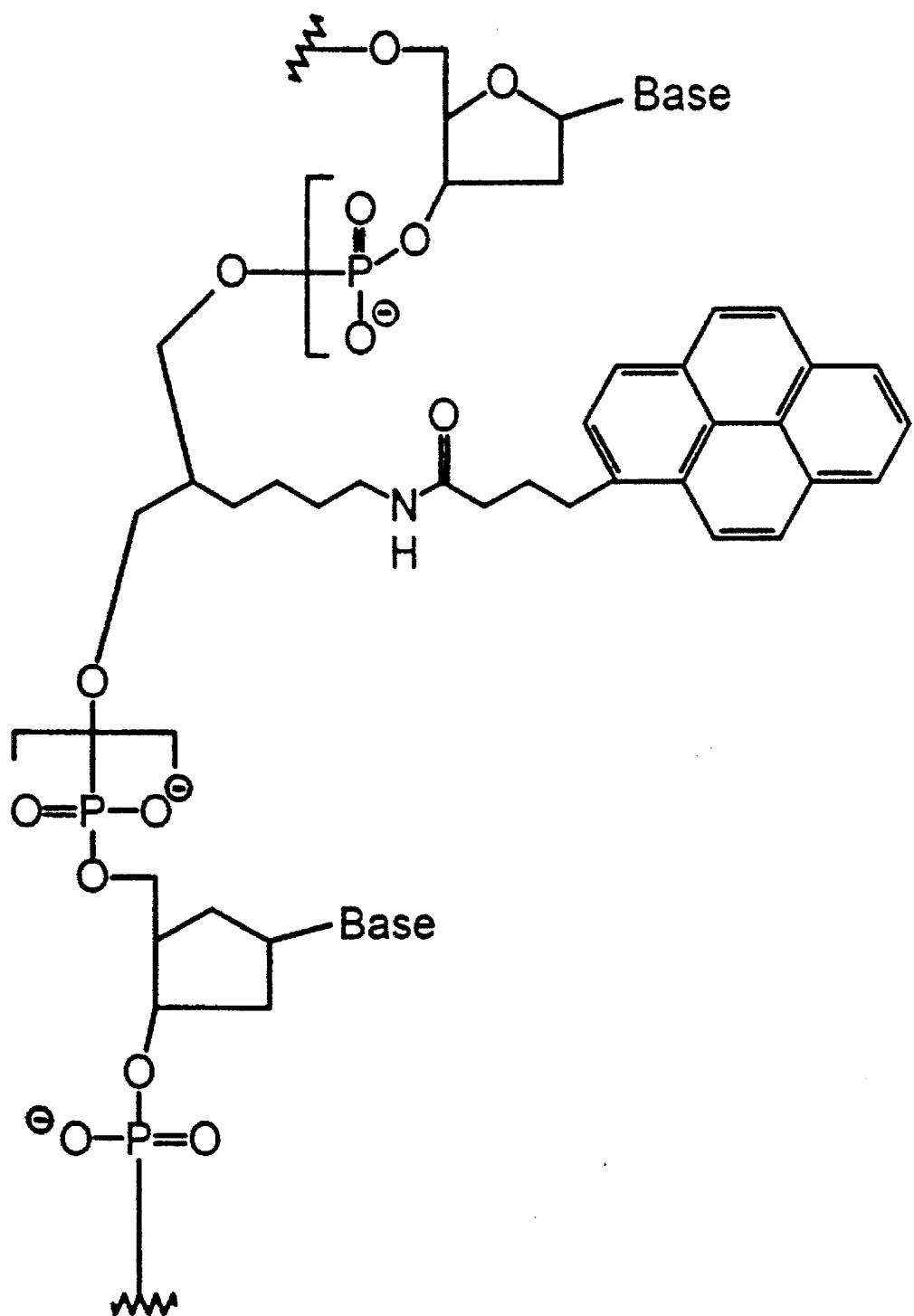
FIG. 3 shows a structure of a DNA oligomer labeled with the deoxyribose base removed and replaced by a carbon chain.
Figure 4:
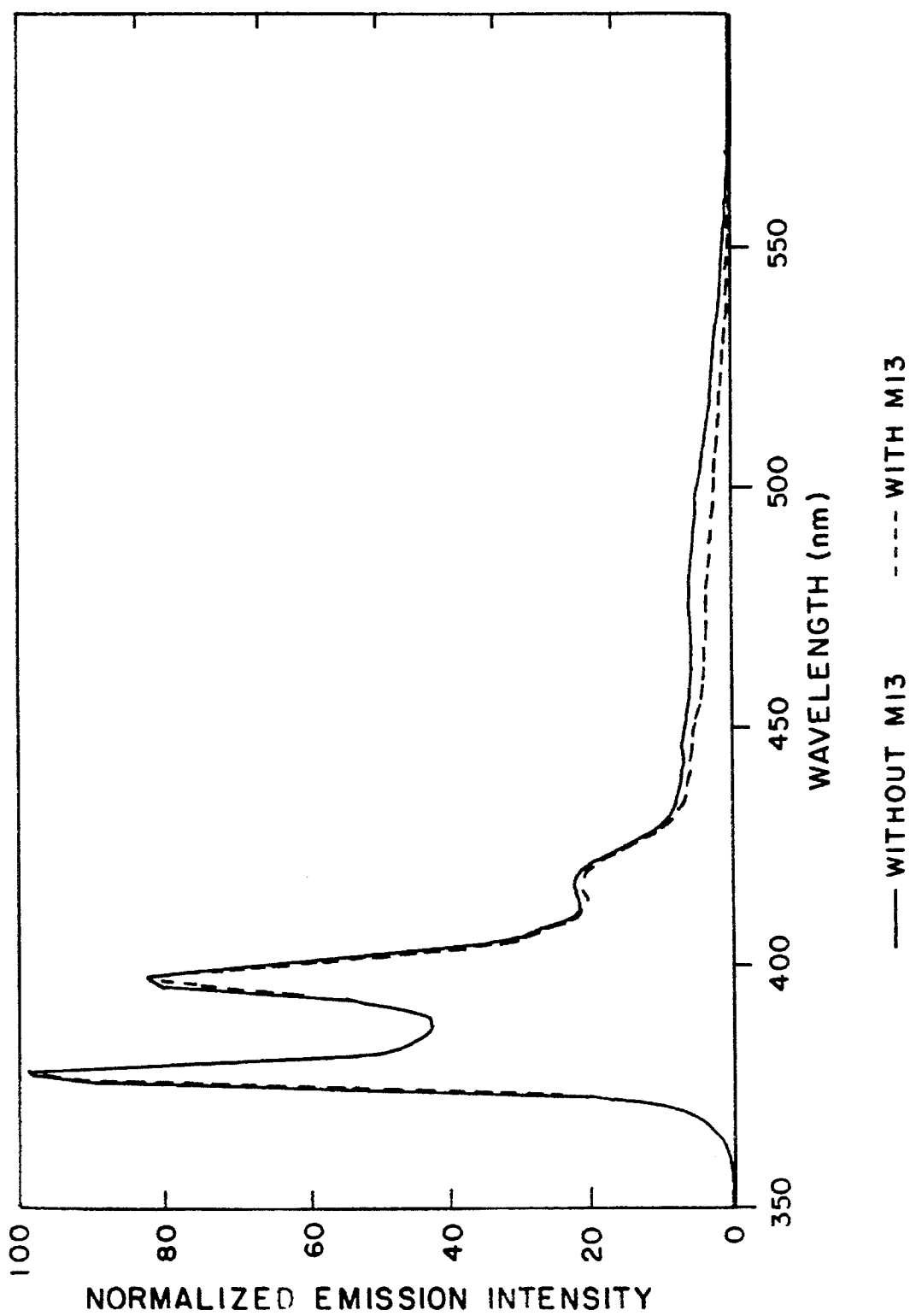
FIG. 4 shows two fluorescent spectra of an oligomer, labeled as in FIG. 3, with and without the complementary DNA strand present, demonstrating production of an excimer. The spectra were normalized to the base peak at 378 nm.

To demonstrate the use of PORSCHA for DNA detection, an oligomer was labeled with pyrene as in FIG. 3, with four nucleotide bases between each pair of labels. Oligomers were prepared with this modified nucleotide and purified by HPLC. Preliminary experiments suggested that when the complementary DNA (M13mp18 in this case) was added to the dual labeled oligomer, a change in excimer intensity, as shown in FIG. 4, was observed.

General Procedures for Examples 2 and 3

The Pyrene Acetic Acid-Propane Diamine Linker (PAA-PDA) was prepared as follows: Under argon, with stirring, 1 g of pyrene acetic acid (Aldrich Chemical Co., Milwaukee, Wis.) was dissolved in 50 mL of dimethylformamide. Approximately 1 g of carbonyldiimidazole (Aldrich Chemical Co., Milwaukee, Wis.) was added. The solution was heated to approximately 60° C. for 30 mins. The solution was poured into 200 mL of water containing 5 mL of propane diamine (cooled in ice). A small amount of precipitate formed. HCl was added to redissolve the precipitate and the brown solution decolorized with activated charcoal. The charcoal was removed by filtering through a bed of diatomaceous earth. The solution was made basic with sodium carbonate and cooled. The very fine, tan precipitate that formed was remove by filtration (very slow to filter) and dried under a vacuum. The yield of product was approximately 150 mg of a tan solid.

Aminomethyl Pyrene (as HCl salt) was purchased from Molecular Probes (Eugene, Oreg., catalog number A-2421). Aminoethyl Pyrene (as HCl salt) was prepared by the method of Whaley, et al., J. Organic Chemistry, 19 973–977 (1954)

The pyrene labeled phosphates of the DNA strands were prepared by a variation of the general method of Froehler (Tetrahedron Letters 27 5575–5578 (1986)) or Agrawai and Tang (Tetrahedron Letters 31 1543–1546(1990)) from the corresponding amino pyrenes and produced oligomers with the linkages shown in FIG. 12a through 12c. The amines were dissolved in either dimethylformamide or N-methylpyrrolidinone with N-methylpyrrolidinone preferred. Then 200 mg of triethylamine/100 mg of pyrene amine was added and 1 g of carbon tetrachloride/100 mg of pyrene amine. The solubility of the pyrene amines is approximately 100 mg/4 g solvent. The employment of triethylamine as an acid scavenger allows more efficient use of the less readily available pyrene amine.

Example 2—Labeling of 3' or 5' ends with pyrene

Reagents to label DNA with pyrene at the 3' and 5' ends recently became commercially available. These reagents were purchased from Peninsula Laboratories, Inc. (Belmont, Calif.) and were used as per manufacturer's instructions. The 5' end is labeled with a phosphoramidite reagent (catalog number N4347). This reagent produces DNA (after deprotection) with a label whose structure is shown in FIG. 13a. The 3' end is labeled by starting with controlled pore glass labeled with pyrene (catalog number N4048). This produces DNA (after deprotection and cleavage) with a label whose structure is shown in FIG. 13b. The product was purified on a Pharmacia (Piscataway, N.J.) NAP column (catalog number 17-0854-02) as per manufacturer's instructions.

Example 3—Purification of oligomers

The oligomers were cleaved from the solid support with 1–2 mL of concentrated ammonium hydroxide as per the manufacturer's instructions. The product was purified by HPLC by injecting 50–100 µL of the ammonium hydroxide solution into a 4.5×250 mm, polymeric C18 reverse phase HPLC column. A gradient of 0–90% A:B over 20 minutes was started after 1 minute with a flow of 1 mL/min. 0.025M phosphate. pH 6 was used for solution A and acetonitrile was used for solution B. The fractions showing pyrene absorptions bands in the UV at 343 were collected and tested. The elution time under these conditions was approximately 10 minutes for all the oligomers. Due to poor labeling efficiency, the oligomers with two pyrene labels showed three peaks upon monitoring the absorbance at 260 nm corresponding to oligomers labeled with 0, 1, and 2 pyrene labels. Generally, only the oligomers with the two pyrene labels were collected. Also, due to the optical centers created by the phosphoramide linkage, the peaks were generally broad and sometimes showed fine structure indicating partial separation of the diasteriomers. Several fractions were usually collected and tested separately. The results were often indistinguishable for the various fractions.

General procedure for observing pyrene fluorescence in nucleic acid detection

To a 3×3 ID fluorimeter cell, was added 100 µL of buffer and 1–10 µL of pyrene labeled oligomer. A SLM8000 spectrofluorimeter, with the excitation set at 343 nm, was used to obtain the spectra. The cell was theromstated with a circulating water bath between 15°–70° C. Generally, either 15° or 25° C. was used to obtain the spectra. The emission spectra from 350–600 nm were obtained at 1 second/point with a 2 nm step interval. The spectra were plotted as A/B with A being the intensity of the emission and B the excitation intensity. After the initial spectrum was obtained, 1–10 µL of surfactant (145 mg/5 mL for all surfactants) was added to the fluorimeter cell, the contents vortexed, and the fluorescent spectrum retaken. The buffer was varied between distilled water, phosphate buffered saline, pH 7, 0.5M phosphate pH 8.3 containing 0.5M sodium chloride, and 2× SSC without appreciable change in fluorescence emission intensity.

Oligomers labeled with two pyrenes are used to observe the excimer and its intensity change upon addition of the complementary stand. The intensity of the pyrene monomer fluorescence at 378 and 96 nm changes with temperature. At higher temperatures the monomer emission decreases relative to the excimer centered at 480 nm.

TABLE 1

Structures and Sequences of Test Strands
Structures of linkers and labels are shown in FIGS. 12a–c and 13a and 13b

| Code Name | Sequence |
| --- | --- |
| M13-3M (PAA-PDA) | 5'-TGGTCATAGCpGTpTCCTGT-3' (SEQ ID NO: 1) |
| M13-1MC(PMA) | 5'-TGGTCATAGCTGppTCCTGT-3' (SEQ ID NO: 2) |
| TA-F1A(PEA) | 5'-CGCCAAGCTATppAGGTGACACT-3' (SEQ ID NO: 3) |
| M13-4M1 (Pyrene CEP) | 5'-xGTGAAATTGTTATCCGCT-3' (SEQ ID NO: 4) |
| M13-2M1 (Pyrene CPG) | 5'-TGGTCATAGCTGTTTCCTGTGx-3' (SEQ ID NO: 5) | x = 5' or 3' Pyrene label
p = Pyrene labeled phosphate attached to deoxythymidine Obviously, many modifications and variations of the present invention are possible in light of the above teachings. It is therefore to be understood that, within the scope of the appended claims, the invention may be practiced otherwise than as specifically described.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single stranded
( D ) TOPOLOGY: linear ( i i ) MOLECULE TYPE: Other nucleic acid ( i i i ) HYPOTHETICAL: no ( i v ) ANTI-SENSE: no ( x i ) SEQUENCE DESCRIPTION: SEQ ID NO: 1:

TGGTCARAGC TGTTTTCCTGT       20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single stranded
        ( D ) TOPOLOGY: linear ( i i ) MOLECULE TYPE: Other nucleic acid ( i i i ) HYPOTHETICAL: no ( i v ) ANTI-SENSE: no ( x i ) SEQUENCE DESCRIPTION: SEQ ID NO:2:

TGGTCATAGC TGTTTCCTGT       20

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single stranded
        ( D ) TOPOLOGY: linear ( i i ) MOLECULE TYPE: Other nucleic acid ( i i i ) HYPOTHETICAL: no ( i v ) ANTI-SENSE: no ( x i ) SEQUENCE DESCRIPTION: SEQ ID NO:3:

CGCCAAGCTA TTTAGGTGAC ACT       23

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single stranded
        ( D ) TOPOLOGY: linear ( i i ) MOLECULE TYPE: Other nucleic acid ( i i i ) HYPOTHETICAL: no ( i v ) ANTI-SENSE: no ( x i ) SEQUENCE DESCRIPTION: SEQ ID NO:4:

GTGAAATTGT TATCCGCT       18

( 2 ) INFORMATION FOR SEQ ID NO:5:

( i ) SEQUENCE CHARACTERTISTICS:
        ( A ) LENGTH: 21 base pairs
        ( B ) TYPE: nucleic acid
        ( C ) STRANDEDNESS: single stranded
        ( D ) TOPOLOGY: linear ( i i ) MOLECULE TYPE: Other nucleic acid ( i i i ) HYPOTHETICAL: no ( i v ) ANTI-SENSE: no ( x i ) SEQUENCE DESCRIPTION: SEQ ID NO:5:

TGGTCAAGC TGTTTCCTGT G                                                                    2 1

What is claimed is:

1. A method for detecting the presence of a target polynucleic acid strand having a specified nucleotide sequence in an aqueous matrix suspected of including said target polynucleic acid strand, comprising the steps of:

adding to the matrix a strand of polynucleic acid at least substantially complementary to said target polynucleic acid strand, said at least substantially complementary polynucleic acid strand having attached thereto, at least two labels comprising fluorophore moieties, each attached to a corresponding internucleotide phosphate group, or between the phosphorus atoms of said at least substantially complementary polynucleic acid, so that when said at least substantially complementary polynucleic acid strand is not bound with said target polynucleic acid strand, said at least two fluorophore moieties are significantly more likely to electronically interact with each other to form an excimer and thus vary the wavelength dependance of their spectra than they would be if said at least substantially complementary polynucleic acid strand were bound to said target polynucleic acid, each of said at least two fluorophore moieties including at least one polycyclic aromatic groups;

adding a quaternary ammonium surfactant having an at least C4 alkyl chain to said aqueous matrix in a concentration that significantly enhances the fluorescence of said fluorophore moieties or said excimer; and detecting said variation in the emission or absorption spectra, wherein said variation in the emission or absorption spectra indicates the presence of said target polynucleic acid strand.

2. The method of claim 1, wherein said variation occurs in the emission spectra of said fluorophore moieties.

3. The method of claim 1, wherein said variation occurs in the absorption spectra of said fluorophore moieties.

4. The method of claim 1, wherein each of said at least two labels is attached to its corresponding internucleotide phosphate group by a linker.

5. The method of claim 4, wherein the linker is soluble in said matrix and is between 1 and 1300 atoms long.

6. The method of claim 1, wherein each of said-at least two labels is a fluorescent dye.

7. The method of claim 6, wherein each of said at least two labels includes a pyrene ring, a napthalene ring or an anthracene ring.

8. A method for detecting the presence of a target polynucleic acid strand having a specified nucleotide sequence in a matrix suspected of including said target polynucleic acid strand, comprising the steps of:

adding to the matrix a strand of polynucleic acid at least substantially complementary to said target polynucleic acid strand, said at least substantially complementary polynucleic acid strand having attached thereto, at least two labels comprising fluorophore moieties, each attached to a corresponding internucleotide phosphate group and spaced sufficiently close together along said at least substantially complementary strand so that when said substantially complementary polynucleic acid is bound with said target polynucleic acid strand, said at least two fluorophore moieties are significantly more likely to electronically interact with each other to form an excimer and thus vary the wavelength dependance of their spectra than they would be if said at least substantially complementary polynucleic acid strand were unbound to said target polynucleic acid strand; and adding a quaternary ammonium surfactant having an at least C4 alkyl chain to said matrix in a concentration that significantly enhances the fluorescence of said fluorophore moieties or said excimer, each of said at least two fluorophore moieties including at least one polycyclic aromatic groups; and detecting said variation in the emission or absorption spectra, wherein said variation in the emission or absorption spectra indicates the presence of said target polynucleic acid strand.

9. The method of claim 8, wherein said variation occurs in the emission spectra of said fluorophore moieties.

10. The method of claim 8, wherein said variation occurs in the absorption spectra of said fluorophore moieties.

11. The method of claim 10, wherein each of said at least two labels is attached to its corresponding internucleotide phosphate group by a linker.

12. The method of claim 11, wherein the linker is soluble in said matrix and is between 1 and 1300 atoms long.

13. The method of claim 11, wherein each of said at least two labels includes a pyrene ring, a napthalene ring or an anthracene ring.

14. A method for the detection of a target nucleic acid strand, comprising the steps of:

(a) labeling a strand of nucleic acid at least substantially complementary to said target strand with a polycyclic aromatic fluorophore;

(b) determining the fluorescent emission intensity of said labeled at least substantially complementary strand, in the presence of a quaternary ammonium salt surfactant having at least one C4 or greater alkyl chain, and in the absence of said target strand;

(c) mixing said target strand and said labeled at least substantially complementary strand to form a mixture, under conditions permitting selective binding of said target strand to said labeled at least substantially complementary strand;

(d) including said quaternary ammonium salt surfactant within said mixture, said quaternary ammonium salt surfactant having a concentration within said mixture sufficient to increase the fluorescent emission of said labeled strand;

(e) detecting any change in fluorescent emission intensity of said labeled strand, whereby an increase in the fluorescent emission intensity of said labeled strand over the fluorescent emission intensity determined in step (b) indicates the presence of said target strand.

15. The method of claim 14, wherein said label is attached to its corresponding internucleotide phosphate group by a linker.

16. The method of claim 15, wherein the linker is between 1 and 1300 atoms long.

17. The method of claim 14, wherein said label includes a pyrene ring, a napthalene ring or an anthracene ring.

18. The method of claim 8, wherein said matrix is an aqueous matrix.

* * * * *